(12) United States Patent
Yang et al.

(10) Patent No.: US 9,592,094 B2
(45) Date of Patent: Mar. 14, 2017

(54) SURGICAL DEVICE AND COMPONENT HAVING MOVABLE PLUG PORTIONS

(75) Inventors: Guang-Zhong Yang, Surrey (GB); Jianzhong Shang, Kent (GB)

(73) Assignee: Imperial Innovations Limited, London (GB)

( * ) Notice: Subject to any disclaimer, the term of this patent is extended or adjusted under 35 U.S.C. 154(b) by 140 days.

(21) Appl. No.: 14/116,640

(22) PCT Filed: May 14, 2012

(86) PCT No.: PCT/GB2012/051069
§ 371 (c)(1),
(2), (4) Date: Feb. 7, 2014

(87) PCT Pub. No.: WO2012/153151
PCT Pub. Date: Nov. 15, 2012

(65) Prior Publication Data
US 2014/0142377 A1    May 22, 2014

(30) Foreign Application Priority Data

May 12, 2011 (GB) .................................. 1107939.9
Jul. 15, 2011 (GB) .................................. 1112228.0

(51) Int. Cl.
*A61B 1/00* (2006.01)
*A61B 19/00* (2006.01)
(Continued)

(52) U.S. Cl.
CPC ........ *A61B 19/2203* (2013.01); *A61B 1/0055* (2013.01); *A61B 1/018* (2013.01);
(Continued)

(58) Field of Classification Search
USPC ......... 600/114, 121–125, 127, 129, 139–145
See application file for complete search history.

(56) References Cited

U.S. PATENT DOCUMENTS 6,106,521 A * 8/2000 Blewett .............. A61B 18/1477
                                                         600/105
6,352,503 B1 * 3/2002 Matsui ............... A61B 1/00071
                                                         600/104
(Continued)

FOREIGN PATENT DOCUMENTS

CN         102018493 A     4/2011
WO    WO 2004/052171 A2    6/2004

*Primary Examiner* — Matthew J Kasztejna
(74) *Attorney, Agent, or Firm* — Blank Rome LLP

(57) ABSTRACT

A surgical device (2) having a distal end and a proximal end, and comprising a delivery portion (12) extending from the proximal end and comprising first and second instrument delivery channels, an active portion (4,8) at a distal portion of the device and a plug (10) having a proximal end and a distal end, and engageable with the delivery portion at its proximal end, and with the active portion at its distal end, the plug comprising first and second plug channels (82) each defining a curved path, such that the plug channels diverge from one another towards the distal end of the plug wherein when the plug is engaged with the delivery portion the first plug channel and the first instrument delivery channel form a first instrument channel and the second plug channel and the second instrument delivery channel form a second instrument channel.

23 Claims, 12 Drawing Sheets

(51) Int. Cl.
*A61B 1/005* (2006.01)
*A61B 1/018* (2006.01)
*A61B 17/00* (2006.01)

(52) U.S. Cl.
CPC .............. *A61B 34/30* (2016.02); *A61B 34/37* (2016.02); *A61B 1/0056* (2013.01); *A61B 90/30* (2016.02); *A61B 90/361* (2016.02); *A61B 2017/0034* (2013.01); *A61B 2017/00278* (2013.01); *A61B 2017/00309* (2013.01); *A61B 2017/00314* (2013.01); *A61B 2017/00327* (2013.01); *A61B 2034/302* (2016.02); *A61B 2034/303* (2016.02); *A61B 2034/306* (2016.02)

(56) References Cited

U.S. PATENT DOCUMENTS

| | | | | |
|---|---|---|---|---|
| 7,621,869 | B2 * | 11/2009 | Ratnakar | A61B 1/00179 600/113 |
| 8,888,687 | B2 * | 11/2014 | Ostrovsky | A61B 1/0008 600/106 |
| 2005/0096502 | A1 * | 5/2005 | Khalili | A61B 1/018 600/106 |
| 2005/0234294 | A1 * | 10/2005 | Saadat | A61B 1/0008 600/104 |
| 2005/0272977 | A1 | 12/2005 | Saadat et al. | |
| 2006/0189845 | A1 * | 8/2006 | Maahs | A61B 1/0008 600/146 |
| 2007/0135803 | A1 | 6/2007 | Belson | |
| 2007/0167680 | A1 * | 7/2007 | Miyamoto | A61B 1/0055 600/106 |
| 2008/0051629 | A1 * | 2/2008 | Sugiyama | A61B 1/00193 600/114 |
| 2008/0071289 | A1 * | 3/2008 | Cooper | A61B 1/00087 606/130 |
| 2008/0269562 | A1 * | 10/2008 | Marescaux | A61B 1/00087 600/142 |
| 2009/0287044 | A1 | 11/2009 | Yamatani | |
| 2010/0036198 | A1 * | 2/2010 | Tacchino | A61B 1/0014 600/106 |
| 2010/0063354 | A1 | 3/2010 | Hashimoto et al. | |
| 2010/0081874 | A1 * | 4/2010 | Miyamoto | A61B 1/00087 600/109 |
| 2010/0198232 | A1 | 8/2010 | Diolaiti | |
| 2011/0065985 | A1 | 3/2011 | Wehrheim | |

* cited by examiner

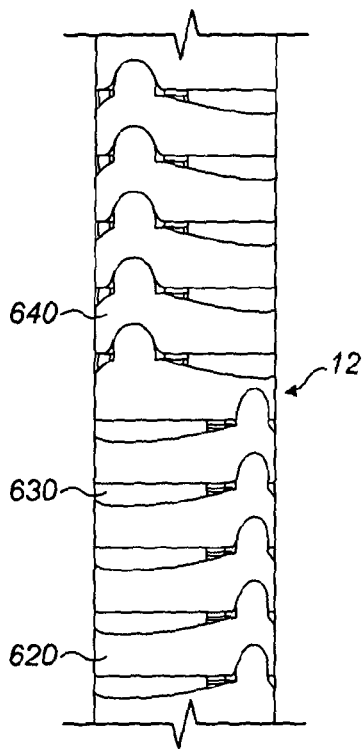 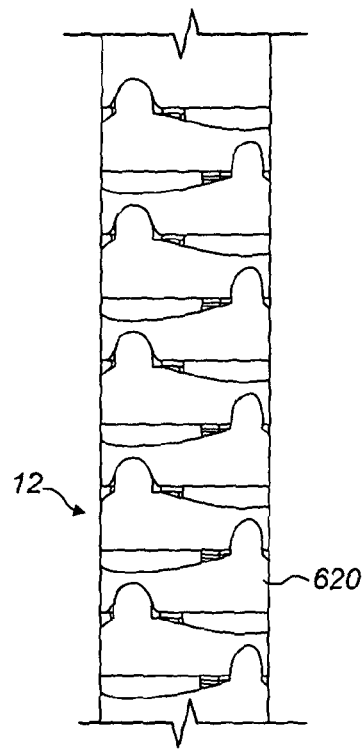
FIG. 9　　　　　FIG. 10
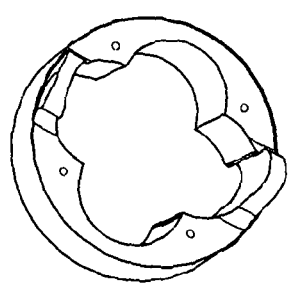 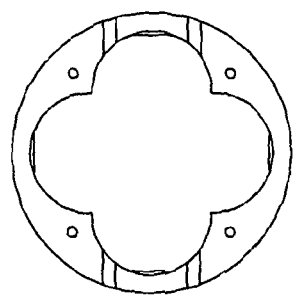
FIG. 11　　　　　FIG. 12

SURGICAL DEVICE AND COMPONENT HAVING MOVABLE PLUG PORTIONS

This invention relates to a surgical device and particularly to a robotic surgical device suitable for use in Minimal Invasive Surgery (MIS).

Since the advent of laparoscopy, surgical technology has advanced on an exponential scale that has broadened the accessibility of the surgeon to the operative field with minimal incisions. MIS is usually carried out through natural body openings or small artificial incisions, resulting in reduced patient trauma, shortened hospitalisation, improved diagnostic accuracy and therapeutic outcome. The technique, however, requires significantly higher dexterity from the surgeons due to the loss of depth perception (because the images are usually captured and displayed on a 2D monitor), reduced tactile feedback, and increased complexity of instrument control. Current instruments are difficult to operate, due to the use of long, rigid, ergonomically unnatural instruments associated with the "fulcrum effect", necessitating movements by the surgeon's hand in counter-intuitive ways.

The introduction of robotic assisted MIS has addressed many of the problems stated above, particularly with the introduction of 3D vision, integrated instrument control, motion scaling, and alignment of visual-motion axis.

Known systems incorporate a master unit where the surgeon views the surgical field through a magnified 3D display, and the surgeon's hand movements are digitally replicated to the small robotically controlled endo-wrists operating inside the patient, enabling articulated movement of the instrument tip similar to that of the human. The digital interface also filters out the surgeon's tremor and scales it down to the slave system that carries out on the operative field.

In MIS, most surgical tools use a rigid shaft with a roll-pitch-yaw mechanism for providing three degrees of rotational movements to an end-effector. Although the fine manipulation capabilities of a MIS robot in augmenting machine precision in performing scaled down, steady, tremor-free motion are well appreciated, the application of a MIS robot to complex procedures that involve curved anatomical pathways is still limited. In surgery, the pursuit of even less invasive procedures through the use of natural orifices (e.g. NOTES—Natural Orifice Transluminal Endoscopic Surgery) or single port (e.g. SILS—Single Incision Laparoscopic Surgery) has called for the development of flexible instruments that can follow curved anatomical pathways, whilst providing a stable operating environment with interchangeable instrument channels and integrated vision/imaging.

Whether in respect of NOTES or SILS, the move towards the use of flexible instruments integrated with surgical instruments represents the current paradigm shift of flexible access minimally invasive surgery, where the selection of an incision point is no longer dictated by anatomical access but rather by safety, cosmetic, and patient choices.

Thus far, most of the NOTES or SILS procedures are performed by adapting existing flexible endoscopes. Existing endoscopes have been designed with maximum flexibility for exploring the gastrointestinal tract and there is no active control of the stability of the tip of the endoscope for interventional procedures because the narrow gastrointestinal track acts as an external constraint to impose the stability and fixation during endoscopic procedures. The flexible endoscope is therefore a much more difficult instrument to navigate inside the peritoneal cavity. The Natural Orifice Surgery Consortium for Assessment and Research (NOSCAR), a joint initiative supported by the American Society for Gastrointestinal Endoscopy (ASGE) and the Society of American Gastrointestinal and Endoscopic Surgeons (SAGES) has identified 12 fundamental challenges to the safe introduction of NOTES. These include access, closure, infection control, suturing, spatial orientation and management of iatrogenic intraperitoneal complications, as well as training and new device development. In terms of providing access and safe operating environment, the provision of manoeuvrability, stability and triangulation are important considerations and current endoscopes do not satisfy most of these requirements.

Thus far, a number of dedicated NOTES navigation platforms have been developed, most of which are based on the adaptation of existing endoscopes with controlled flexibility and multiple instrument passage.

According to a first aspect of the invention there is provided a surgical device having a distal end and a proximal end, and comprising a delivery portion, extending from the proximal end and comprising first and second instrument delivery channels, an active portion at a distal portion of the device, and a plug having a proximal end and a distal end, and engageable with the delivery portion at its proximal end, and with the active portion at its distal end, the plug comprising first and second plug channels each defining a curved path, such that the plug channels diverge from one another towards the distal end of the plug, wherein when the plug is engaged with the delivery portion, the first plug channel and the first instrument delivery channel form a first instrument channel and, the second plug channel and the second instrument delivery channel form a second instrument channel.

According to a second aspect of the present invention there is provided a component for a surgical device, the component comprising a delivery portion comprising first and second instrument delivery channels extending through the delivery portion, and a plug engageable with the delivery portion at a proximal end of the plug, which plug comprises first and second plug channels each defining a curved path, such that the plug channels diverge from one another towards a distal end of the plug when the plug is engaged with the delivery portion, and wherein the first plug channel and the first instrument delivery channel form a first instrument channel and the second plug channel and the second instrument delivery channel form a second instrument channel.

In embodiments of the invention, the component may further comprise an active portion engageable with a distal end of the plug to form a device in which the delivery portion extends from a proximal end of the device, and the active portion forms a distal portion of the device.

The first and second instrument delivery channels are adapted to carry first and second instruments respectively and when the plug is engaged with the delivery portion, the first and second plug channels are also adapted to carry the first and second instruments respectively.

When the plug is engaged with the delivery portion to form first and second instrument channels, each of the first and second instrument channels is adapted to carry first and second instruments respectively.

By means of the present invention it is possible to readily connect the delivery portion with the active portion by means of the plug.

As the first and second plug channels extend through the plug towards the distal end of the plug, they adopt a curved configuration and each of the channels curves away from the axis of the plug and therefore from the other channel. The channels thus diverge from one another and cause an instrument passing through a respective plug channel to also adopt a curved path.

This is an important feature of the invention since it means that the orientation of the first and second instrument channels relative to one another and to the device as a whole is determined by the curve of first and second plug channels. This in turn determines the orientation of the first and second instruments carried by the first and second instrument channels respectively.

In some embodiments of the invention the tangential line of the exit of each channel is designed to be 20° relative to the axis of the delivery portion. This angle provides necessary triangulation for the first and second instruments during use of the device.

In some embodiments, the delivery portion may comprise first and second plug portions, the first plug portion comprising the first plug channel, and the second plug portion comprising the second plug channel.

In such embodiments, the plug is split longitudinally into the first and second plug portions.

The first and second plug portions are adapted to fit together to form the plug.

In some embodiments, each plug portion may have a substantially flat face, which face may be caused to abut with the flat face of the other plug portion to form the plug.

The plug portions may be held together in any convenient manner such by use of fasteners, clips or the like.

In use the plug portions may be moveable, or translatable, relative to one another, thus allowing independent movement and/or positioning of the first and second instruments carried by the first an second plug channels respectively.

The movement may be axial movement.

The first and second instrument channels may accommodate first and second instrument arms respectively. Each instrument arm may take any convenient form, but in some embodiments, each instrument arm comprises three sections; a distal section with two directional flexibility and actuatable in two planes; a middle section with one directional flexibility; and a proximal section.

The middle section of each instrument arm is adapted to follow the curved path of the plug channel, and the proximal section of each instrument arm will extend along the instrument delivery channel at the proximal end of the device.

Each instrument arm may take any convenient form, but in some embodiments may be made from a superelastic Nitinol tube driveable by at least one tendon attachable to a distal end of a respective instrument arm and extending along the arm to the proximal end thereof.

Each instrument arm may be actuated by a plurality of tendons for bidirectional actuation.

The tendons may be driven by one or more motors, such as DC motors.

By means of embodiments the invention, it is possible to deliver a first instrument arm and a second instrument arm from the proximal end of the device to the distal end through the first and second instrument channels respectively. In order to position each of the first and second instrument arms appropriately, each instrument arm is inserted into the device at the proximal end thereof such that it advances through a respective instrument channel, first through the delivery portion, and then through the plug to then protrude from the distal end of the plug.

An instrument arm is appropriately positioned once its middle flexible section is located within a respective plug channel and its distal end protrudes from the plug. At this point the distal end of a respective instrument arm is ready to be actuated.

First and second instruments may then be inserted in to the first and second instrument arms respectively and may be advanced through the device within a respective instrument arm until a portion of each instrument protrudes from the distal end of a respective instrument arm.

By means of the plug it is possible therefore to ensure that the first and second instruments are appropriately positioned when deployed so that the required triangulation is achieved during minimally invasive surgery.

A further advantage of the invention is that it is possible to readily remove instruments for cleaning purposes, and/or to deploy different instruments appropriate for a procedure to be carried out.

In particular, in certain embodiments of the invention, each instrument arm may accommodate an interchangeable instrument.

The term "interchangeable instrument" is used herein to define an instrument that may be readily inserted and removed from an instrument arm of a surgical device according to an embodiment of the invention in order that an appropriate instrument may be positioned in an instrument arm for use during a surgical procedure.

In embodiments of the invention, each interchangeable instrument may be flexible but at the same time may be capable of delivering torque.

The torque may be delivered in any desirable way, and may for example be delivered using a hollow flexible multi-headed shaft forming part of the interchangeable instrument.

In some embodiments of the invention, the delivery portion may further comprise a third instrument delivery channel, and the plug may further comprise a third plug channel, the third instrument delivery channel, and the third plug channel forming a third instrument channel when the plug is engaged with the delivery portion.

The third delivery channel enables further devices, such as small instruments to be delivered to the active portion of the device.

In some embodiments in the invention, the apparatus may comprise as an alternative, or in addition to the third instrument channel, a further delivery channel formed in the delivery portion. In such embodiments the plug may comprise a further plug channel, the further delivery channel and the further plug delivery channel form a device channel.

The device channel may be used to deliver, for example signal/power wires through the device.

The active portion may comprise a deployment section and an articulated section.

This articulated section may take any convenient form, but in some embodiments comprises a plurality of articulated universal joints or/and single degree of freedom joints. The articulated section may have one or more micromotors embedded in one or more or all of the joints.

An active portion of the type described hereinabove is described in more detail in our co-pending International patent application filed on the same date the contents of which are incorporated herein by reference.

The deployment section may take any convenient form, for example, a parallel mechanism, but in some embodiments, the deployment section comprises a plurality of joints pivotally linked to one another to form a continuous flexible section.

The flexible section may comprise one or more tendons to drive the flexible section between a non-deployed position in which the flexible section extends substantially in the same plane as that of the delivery portion, and a shifted, deployed position in which the flexible section extends away from the plane of the delivery portion and of the removable instruments.

The flexible section may be adapted to carry a camera at a proximal end thereof. This provides a broad view of an operation site.

The flexible section may also carry one or more light sources along its length to provide additional illumination.

In the deployed position, the tendons may be used to move the flexible section into an S-bend configuration known as a goose-neck. Such an S-bend configuration results in any cameras and light sources being carried by the flexible section being exposed to the site at which the removable instruments will be operated thus further facilitating illumination of that site.

In some embodiments of the invention there may be two structural hard limits corresponding to the non-deployed position, and the deployed position. These hard limits facilitate accurate control of the flexible section and particularly facilitate control of movement of the flexible section between a straight non-deployed position and a maximum bend or deployed position, which, in many cases are the two most desired positions for the flexible section. However, the flexible section may be locked at any desired position between these two limits.

The locking mechanism may take any particular form and may for example comprise a gear system in which the gears are lockable when the flexible section is in the deployed position, or any other desired position.

The delivery portion may take any convenient form, and may for example comprise a hollow shaft.

In some embodiments of the invention, the delivery portion may be flexible.

The flexibility of the delivery portion may be achieved by any convenient means. In some embodiments of the invention, the delivery portion comprises a plurality of links, arranged to allow flexible movement of the delivery portion.

The links may be spaced apart from one another, or may be connected to one another. The links may be pivotably connected to one another.

The delivery portion may further comprise a flexible material adapted to extend between the links.

The delivery portion may be flexible in a single plane only. In other embodiments, the delivery portion may be flexible in more than one plane, and/or sections of the delivery portion may have a different flexibility to other parts of the delivery portion.

In some embodiments of the invention, the rotational axes between any two adjacent links may be arranged in an alternating manner such that orthogonal, or other angles of flexibility are periodically repeated. In such an embodiment, flexible parts of the delivery portion may be bent in any desired direction.

Since the delivery portion is formed from a flexible material interspersed between the links, when the delivery portion is actuated, parts of the flexible material will be compressed while other parts will expand according to the movement of the delivery portion.

In embodiments of the invention in which the delivery portion comprises a hollow shaft having a substantially cylindrical shape, the rotational axis between any two adjacent links is defined by the cylindrical surfaces of the delivery shaft mating in the assembly.

Such an arrangement eliminates the need to have an axle which takes up space and increases the wall thickness of the delivery portion. Further, it enables instruments being carried in the delivery portion to follow an incision path that may not be straight.

The invention will now be further described by way of example only with reference to the accompanying drawings in which:

FIGS. 8 to 10 are partial schematic representations of a portion of delivery portions according to embodiments of the invention resulting in different levels of flexibility of the delivery portion;

FIGS. 11 and 12 are schematic representations showing in more detail a cross-section of the delivery portion and showing a possible link design;

Figure 1:
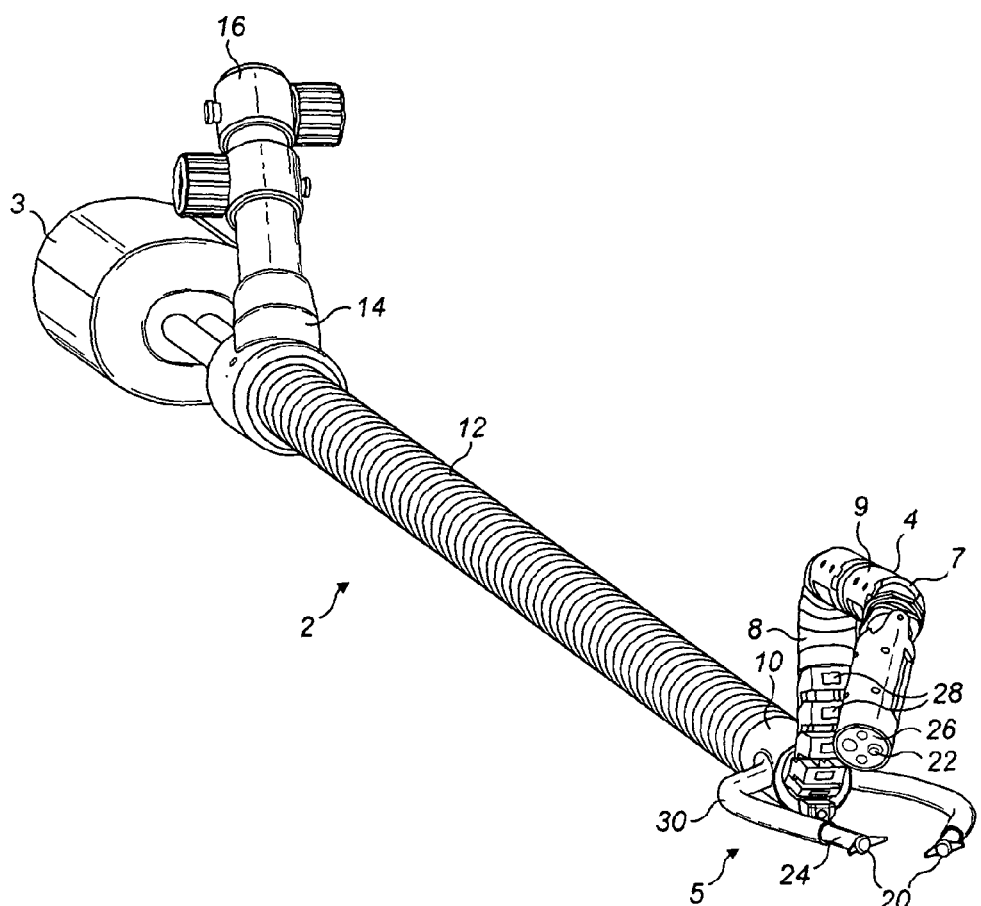
FIG. 1 is a schematic representation of surgical tool according to an embodiment of the invention.

A device according to an embodiment of the invention is shown schematically in FIG. 1 and is designated generally by the reference numeral 2. The device 2 comprises a surgical device suitable for use by a surgeon or other skilled person in minimally invasive surgery.

The device 2 comprises a proximal end 3 and a distal end 5. An active portion of the device comprising an articulated robotic section 4 is formed at the distal end 5 of the device 2 and comprises a tendon driven flexible section 8. During use of the device, a surgeon manipulates the active portion remotely in order to carry out MIS. The device 2 further comprises a delivery portion comprising a hollow shaft 12, a back interface unit 14, and a plug 10 forming an interface between the active portion and the delivery portion. As will be described in more detail below, the delivery portion delivers signals, wires and instruments, for example, to the active portion of the device 2 in order that the active portion may be operated remotely. The plug 10 serves to connect the delivery portion to the active portion.

A universal joint 7 having multiple degrees of freedom is located at a distal end of the robotic section and allows relative motion between the delivery portion and the active portion.

A yaw joint 9 is located at the proximal end of the robotic section 4 and allows one degree of freedom of movement.

The robotic section can also be formed of two or more universal joints, or any combination of universal joints and single degree of freedom joints.

The active section may, in one embodiment comprise a two degrees of freedom universal joint and a single degree of freedom yaw joint. In such an embodiment, each degree of freedom can be actuated by ±45°.

The purpose of the active section to visualise the operation site or to deliver additional instruments to the site.

This means that the neutral position of the universal joint is arranged to angle downwards by 30°. As a result, the travel range of the universal joint is +15° to −75° in a vertical plane and ±45° in the horizontal plane. The yaw joint may also travel ±45° and therefore the travel range of the articulated robotic section 4 is ±90° horizontally and +15° to −75° vertically in such an embodiment.

In other embodiments, different arrangements may be appropriate.

The device further comprises interchangeable instruments 20 which form part of the active device during deployment of the device.

The active portion of the device further comprises cameras 22, 24 for enabling visualization of the area in which the procedure is carried out within a patient's body, for example. One camera, or group of cameras 22 is located at a distal tip of the articulated robotic section 4, whist the other camera or group of cameras 24 is located at an opposite end of the flexible section 8 to provide a broader view of the operation site.

Illumination is provided by LEDs 26, 28 although of course other light sources could be used if appropriate.

The LEDs 26, 28 may be positioned at any convenient location, and this embodiment are positioned at a proximal end of the flexible section 8, and the distal end of the articulated section respectively.

The device 2 as illustrated in FIG. 1 is shown in a deployed position in which the flexible section 8 of the robotic section 4 is positioned generally above the body of the device 2 and is in the form of a "Goose Neck". Further, the inter-changeable instruments 20 are ready for use.

Before the device 2 is placed in a deployed position, the robotic section 4 may lie substantially in the same plane as the hollow shaft 12, and the inter-changeable instruments 20 may either have not yet been inserted, or if inserted remain within the hollow shaft 12.

Once the device has been inserted into the patient's body, and sufficient workspace has been created, the device may be placed in its deployed position by lifting the flexible section 8 and positioning the instruments 20 so that they are exposed and ready for use.

Each of the components of the device 2 will now be described in more detail with reference to the appropriate drawings.

Figure 2A:
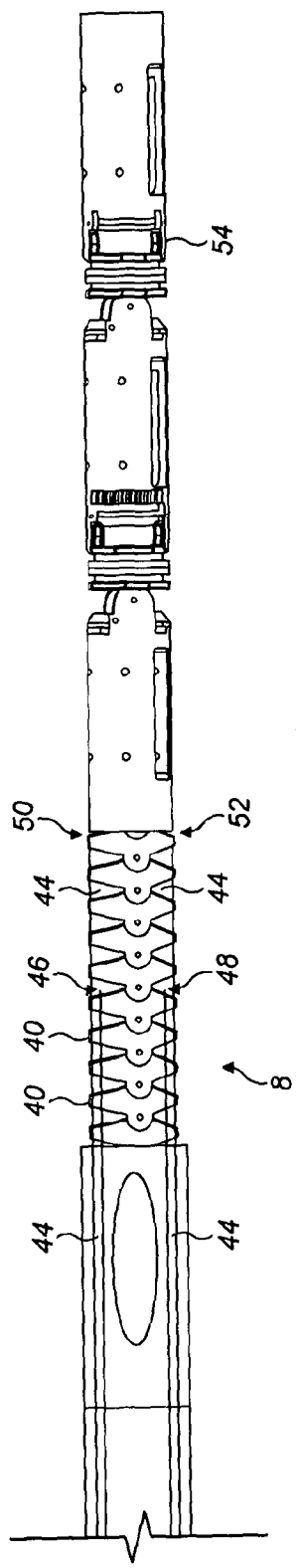
FIGS. 2a and 2b are schematic representations showing details of an articulated robotic section forming part of the device of FIG. 1.
Figure 2B:
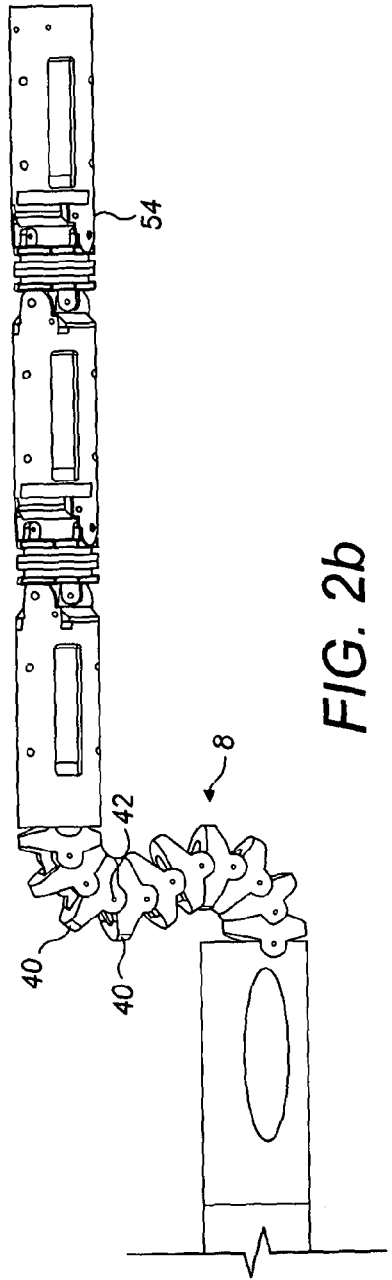

Referring now to FIGS. 2a and 2b the flexible section 8 also known as the "Goose Neck" is shown in more detail. In FIG. 2a the flexible section 8 is in the un-deployed position, and in FIG. 2b it is in the deployed position. The flexible section 8 comprises a plurality of modules 40 linked together by pivot pins 42 joining two adjacent modules 40.

The device 2 further comprises tendons 44, which extend from the tendon driving unit 16 to the flexible section 8 for driving the flexible section 8. A first pair of tendons 44 extends to fixation points 46, 48 on the flexible section 8; whilst a second pair of tendons 44 extends to fixation points 50, 52 also on the flexible section. As can be seen from FIG. 2a particularly, the fixation points 46, 48 are located in a middle portion of the flexible section 8, and the fixation points 50, 52 are located at a distal end of the flexible section 8.

By actuating the two pairs of tendons individually, an "S" shape may be formed. This lifts the distal section 54 of the device 2 creating the so called "Goose Neck", and placing the device in the deployed position.

Figure 3:
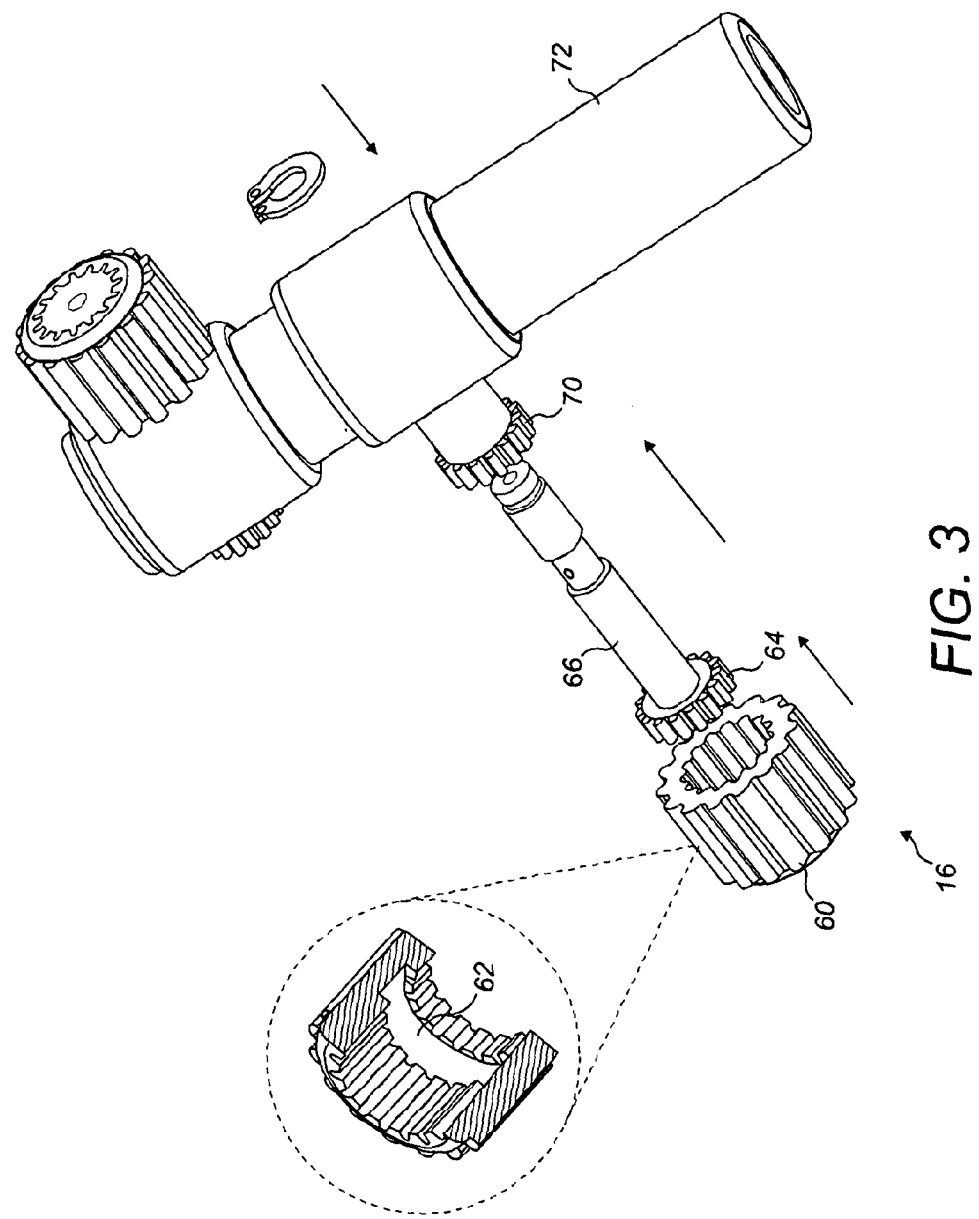
FIG. 3 is a schematic representation showing more details of a drive unit forming part of the device of FIG. 1.

Referring now to FIG. 3, the tendon driving unit 16 is shown in more detail. The driving unit comprises a plurality of sub-units that each drives one pair of tendons. One sub unit is described in more detail with reference to FIG. 3. The sub-unit comprises a driving knob 60 a first gear 64 attached to a driving rod 66, and a second gear 70 attached to a body 72 of the unit 16. As can be seen from the Figures, there is a gap 62 along the teeth of the knob 60. This means that any gear positioned in the knob and located in this gap will be disengaged. The dimensions of the knob and the dimensions and positions of the gears 64, 70 are such that when the driving knob is engaged with the gear 64 the gear 70 will be located in the gap and will therefore be disengaged. This means that the rod 66 will rotate with the driving knob. As a result it drives the tendons 44 which are wrapped around the rod 66 to actuate the flexible section 8 and to place it to the deployed position shown in FIG. 2b.

If the driving knob 60 is driven further in, both the gear 64 and gear 70 are engaged with the knob. Because the gear 70 is attached to the body 72 of the driving unit 16, the rod 66 and the driving knob 60 are locked with the gear 70. This results in the flexible section being locked.

In further embodiments of the invention, there may be more than two pairs of tendons 44, which may terminate at different locations to create multiple bends.

In some embodiments of the invention, by arranging the axle in other planes, 3D bends can be created.

In some embodiments of the invention the knob 60 is replaced by a motor which drives the flexible section 8. In some embodiments there may be a plurality of motors.

Figure 4A:
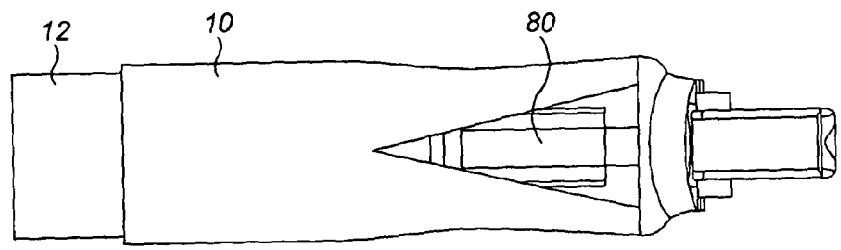
FIG. 4a is a schematic representation of a plug forming part of the device of FIG. 1 showing details of the path along which motor and signal wires extend.
Figure 4B:
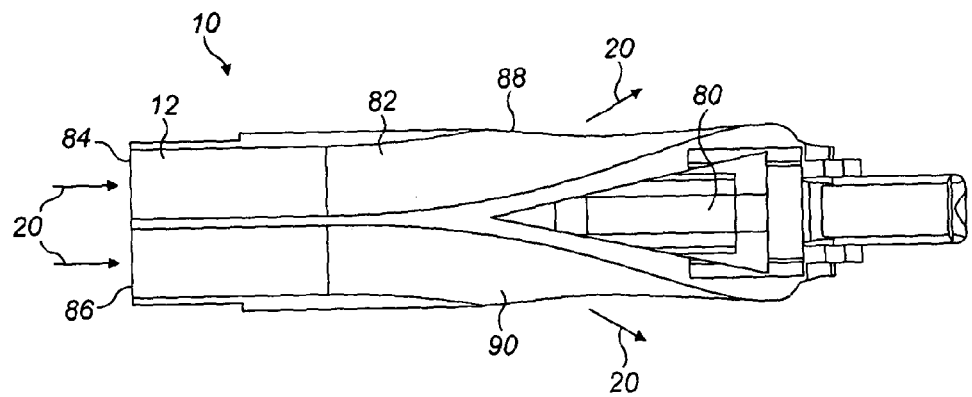
FIG. 4b is schematic representation of the plug shown in FIG. 4a showing details of two instrument channels extending along the plug.
Figure 4C:
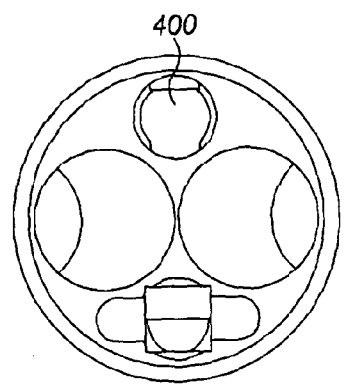
FIG. 4c is a cross section representation of the plug of FIG. 4a showing an additional channel.

Turning now to FIGS. 4a, 4b and 4c the plug 10 is shown in more detail.

The plug 10 serves to connect the delivery portion to the active portion and provides a path 80 in the form of a flexible internal channel, for the motor and signal wires to extend along to connect the motor to the flexible section 8.

The plug 10 also provides triangulation for the inter-changeable instruments 20, which are inserted from the back interface unit 14 and run along side each other within the hollow shaft 12 until they arrive at the plug 10. At the plug, the instruments 20 are split by means of two curved channels 82 formed within the plug 10. The instruments enter the plug 10 from the hollow shaft 12 at inlets 84, 86 and emerge from outlets 88, 90 along a curved trajectory thus providing the desired triangulation.

As shown in FIG. 4c, the plug further comprises a further channel 400 which forms a path for various endoscopic instruments.

Figure 5:
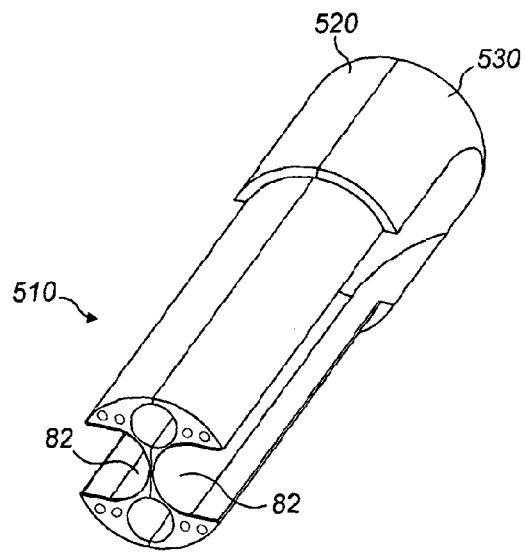
FIG. 5 is a schematic representation of a plug according to another embodiment of the invention and formed from two plug portions.
Figure 6:
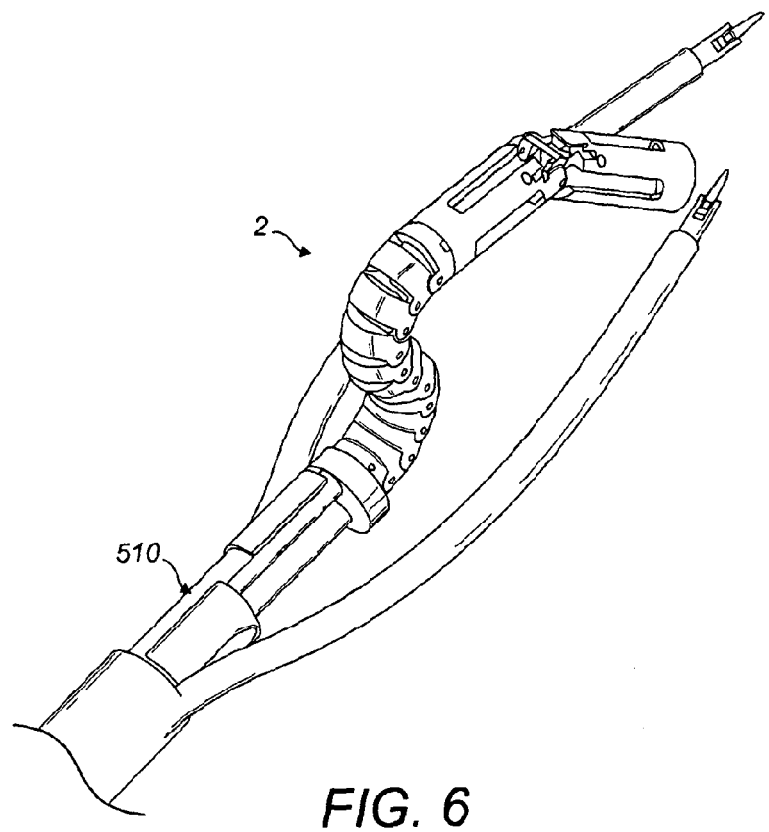
FIG. 6 is schematic representation showing how axial translation of one plug portion relative to the other of the plug shown in FIG. 5 can result in independent movement of instruments carried in the plug.

Turning now to FIGS. 5 and 6, a plug according to another embodiment in the invention is designated generally by the reference numeral 510. In this embodiment the plug 510 comprises a first plug portion 520 and a second plug portion 530. Each plug portion 520, 530 extends along the length of the plug 510. Further, each plug portion comprises a curved channel 82 along which instruments may extend.

The plug portions 520, 530 are moveable axially relative to one another. The result of this is that the instruments carried in the channels 82 may be positioned axially independently from one another as shown in FIG. 6.

Figure 7:
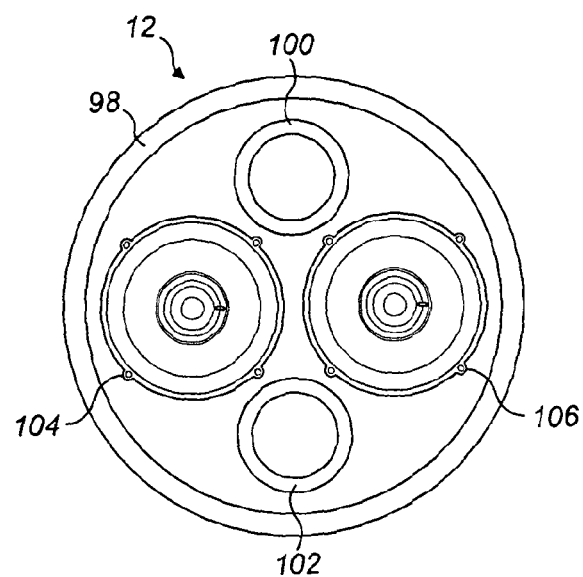
FIG. 7 is a cross section representation of a delivery portion forming part the device of FIG. 1.

Turning now to FIG. 7, the hollow shaft 12 is shown in more detail. The shaft comprises a thin wall 98, two channels 100, 102 and two instrument arms 104, 106.

Channel 100 carries signal, motor power, light source and camera wires and channel 102 forms a path for various endoscopic instruments. Channel 102 aligns with channel 400 of plug 10 described hereinabove and with particular reference to FIG. 4c, thus enabling endoscopic instruments to extend through to the active portion of the device. The instrument arms each carries an inter-changeable instrument.

In some embodiment of the invention the hollow shaft may be formed from a continuous sleeve. In other examples however the shaft may be formed from a plurality of short sections, which may be actuated by tendons in a similar manner to the actuation of the flexible section 8 which has been described herein above.

Such embodiments facilitate navigation of the device around obstacles within a patient's body, and also facilitate the reaching of certain sites that may be difficult to reach without articulation. In a similar manner to that described hereinabove with reference to the flexible section 8, the tendons may be arranged in pairs and each pair may terminate at different location along the hollow shaft 12.

Figure 8:
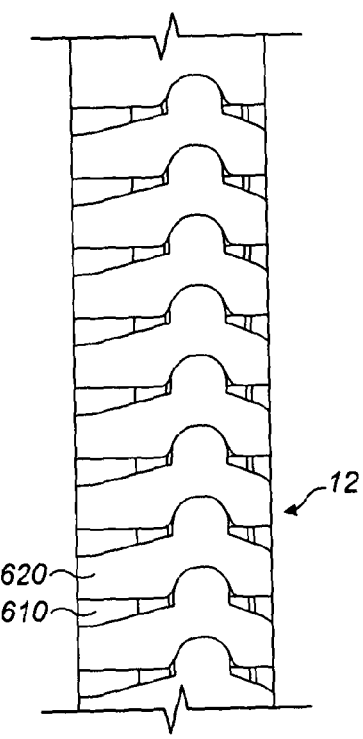
Figure 13:
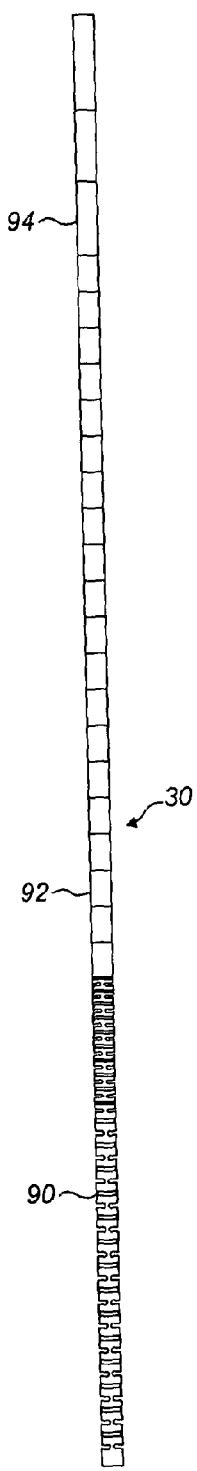
FIG. 13 is a schematic representation of an instrument in the form of an overtube forming part of the device of FIG. 1.

FIGS. 8, 9 and 10 show various embodiments of the invention in which the hollow shaft 12 has different levels of flexibility.

In FIG. 8, the hollow shaft 12 comprises a plurality of links 610 connected to one another, and separated by a flexible material 620.

In FIG. 8, the arrangement of the links is such that the delivery portion is flexible in a single plane only.

In FIG. 9, the delivery portion is flexible in more than one plane, and sections 630, 640 have different levels of flexibility.

In FIG. 10, the delivery shaft has links 610 that are arranged in an alternating manner such that orthogonal, or other angles of flexibility are periodically repeated.

Turning now to FIGS. 13 to 16, parts of the distal portion of the device 2 are shown in more details. As can be seen from these figures in particular, the device 2 comprises instrument arms in the form of sleeves 30 comprising tendon actuated overtubes. Each of the sleeves 30 accommodates one of the inter-changeable instruments 20 such that when the device is in the deployed position at least a tip of each of the interchangeable instruments protrudes from a distal end of a respective sleeve 30. Each overtube extends through the hollow tube 12 along a respective instrument arm to the drive unit 16.

Each sleeve 30 may be made of any convenient material, but in this embodiment the sleeves are made of super elastic Nitinol. A sleeve 30 may be regarded as comprising three sections: a first section 90 extends from the plug 10 and is the distal section from which at least a tip of an interchangeable instrument accommodated in the sleeve will protrude when in the deployed position; a second section 92 that extends through the plug 10; and a third section 94 that extends along the hollow tube 12 to the driving unit.

Each of these sections has different requirements. The first, distal section must be flexible so as not to restrict movement of the instrument carried by it. Cuts 110, 120 are therefore formed in the sleeve in a way to enable the sleeve to be actuated in two orthogonal planes. This results in actuation being possible in any direction by combining the actuating force in the two planes appropriately.

The second section must be able to follow the curved path of a channel 82 in the plug 10 and is cut in one plane. This means that the second section is less flexible than the first section but is still able to curve as required to pass through the plug 10.

The third section is required to be even less flexible but to be able to follow the bend of the external shaft. This section is loosely cut in two planes.

A plurality of tendons (in this case four) in the form of Nitinol wires are attached to the distal end of each sleeve 30 at approximately 90° separation and extend along the overtube 30 to the driving unit 16. Each tendon (not shown) is paired with an opposite tendon. In use, one tendon pulls back while the opposite tendon pays out. This results in the sleeve 30 bending towards the pulling tendon side.

The primary requirement for each sleeve 30 is to combine flexibility in a radial direction with rigidity along an axial direction so that the sleeve is not compressed while it is actuated. This is achieved by means of cut outs which result in a thin wall along the spine (axially) and a thick wall across the sleeve (transversely).

Figure 14:
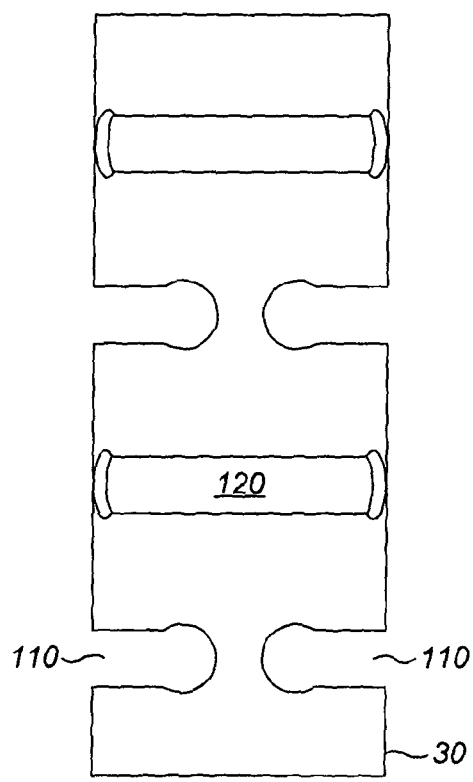
FIG. 14 is a schematic representation showing a portion of the over tube of FIG. 6 forming part of a manipulator that may be used with the device of FIG. 1.

Because the distal section 90 is cut into planes as shown particularly in FIG. 14, there is no backbone to support the structure. This means that the driving of the tendons causes compression along the axis of the overtube 30. By means of the carefully designed cuts 110, 120 in the distal portion of the overtube, axially force may be a relatively thin wall may still be able to withstand the axial forces exerted during use, enabling easy bending. Given a maximum bending of ±90°, the length difference between the compressed edge and the spine is $\delta l = \pi * r / 2$, where r is the radius of the tube. The maximum which is $\delta l$ is the amount of compression when all the slots are completely compressed. Therefore each slot width can be $\delta l / n$ where n is the number of slots in one plane. Using this slot width gives a maximum capability for withstanding the axial forces created when driving the tendons whilst still fulfilling the actuation range requirements of the device.

The results taken from a simulation show that the actuation of one tendon may create a 4N pulling force. This results in approximately 30 mm displacement.

The overtubes 30 may be cut using wire-cut Electrical Discharge Machine.

The instrument tip design varies according to the requirement of the clinical procedure to be carried out.

Figure 15:
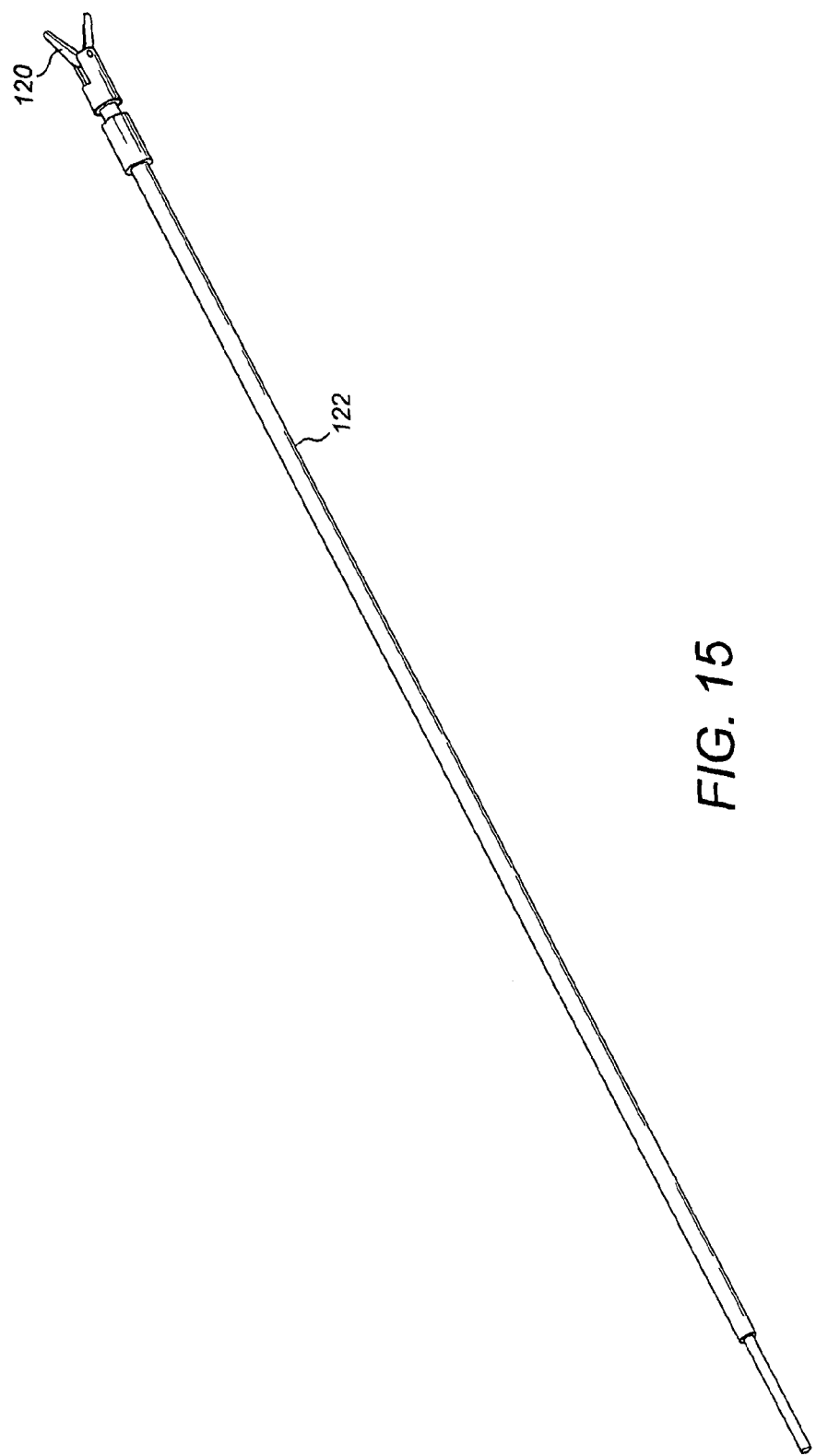
FIG. 15 is a schematic representation of an instrument comprising gripper that may form part of the device of FIG. 1.

A schematic representation of one instrument is shown schematically in FIG. 15. The instrument comprises a gripper 120 that can open and close and rotate about its axis and translate along the sleeve 30.

In the illustrated embodiment the instrument tip is delivered to the distal end of the device for deployment by means of an instrument overtube comprising a flexible hollow shaft 122 which provides the flexibility to follow the sleeve 30 bending, and also to transmit torque to enable the instrument to rotate.

Figure 16:
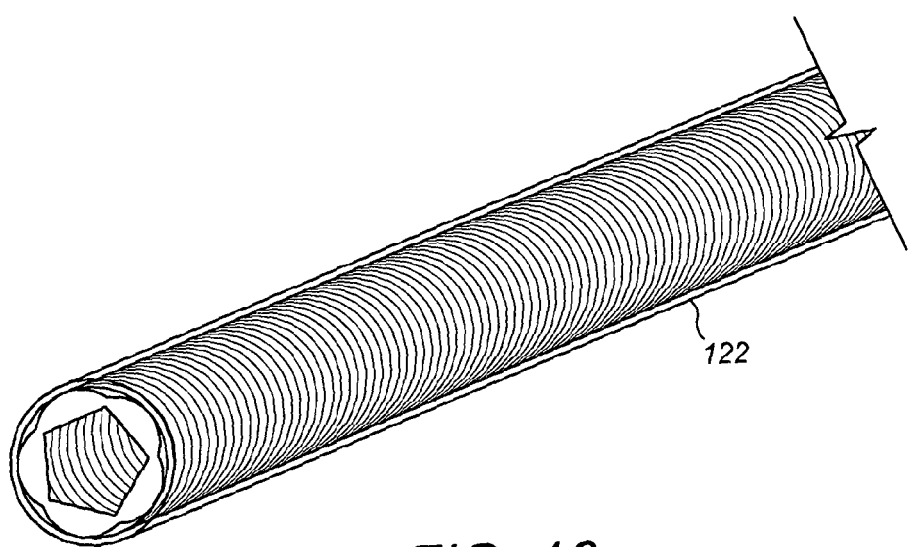
FIG. 16 is a schematic representation of a hollow flexible shaft may be used for the instrument of FIG. 15.

In order to transmit sufficient torque, the hollow shaft 122 is made of multiple wire coil with a flexible coating as shown in FIG. 16. The multiple wire coil significantly improves the torque transmission capability compared with a single wire coil. Further, the flexibility of the shaft is not significantly affected. The flexible coating prevents misplacement of the wires forming the shaft.

The central channel of the flexible shaft provides a path for the tendons actuating the instrument tip.

The gripper also features a section cylindrical feature that is longer than the desired instrument translation stroke within the over tube.

The device according to the invention may be used with any suitable instruments, and particularly with interchangeable instruments which are adapted to be inserted and removed as necessary in order that a surgical procedure may be efficiently and safely carried out.

In general, these instruments should have simple open/closed activation, capable of rotation and translation within the over tube, and have flexibility to be manipulated by the over tubes.

Each of these requirements may be achieved with some basic knowledge of standard laparoscopic instruments or endoscopic instruments. Further design of such instruments is however desirable in order to ensure that the instruments are compatible with the other components of the device.

Figure 17:
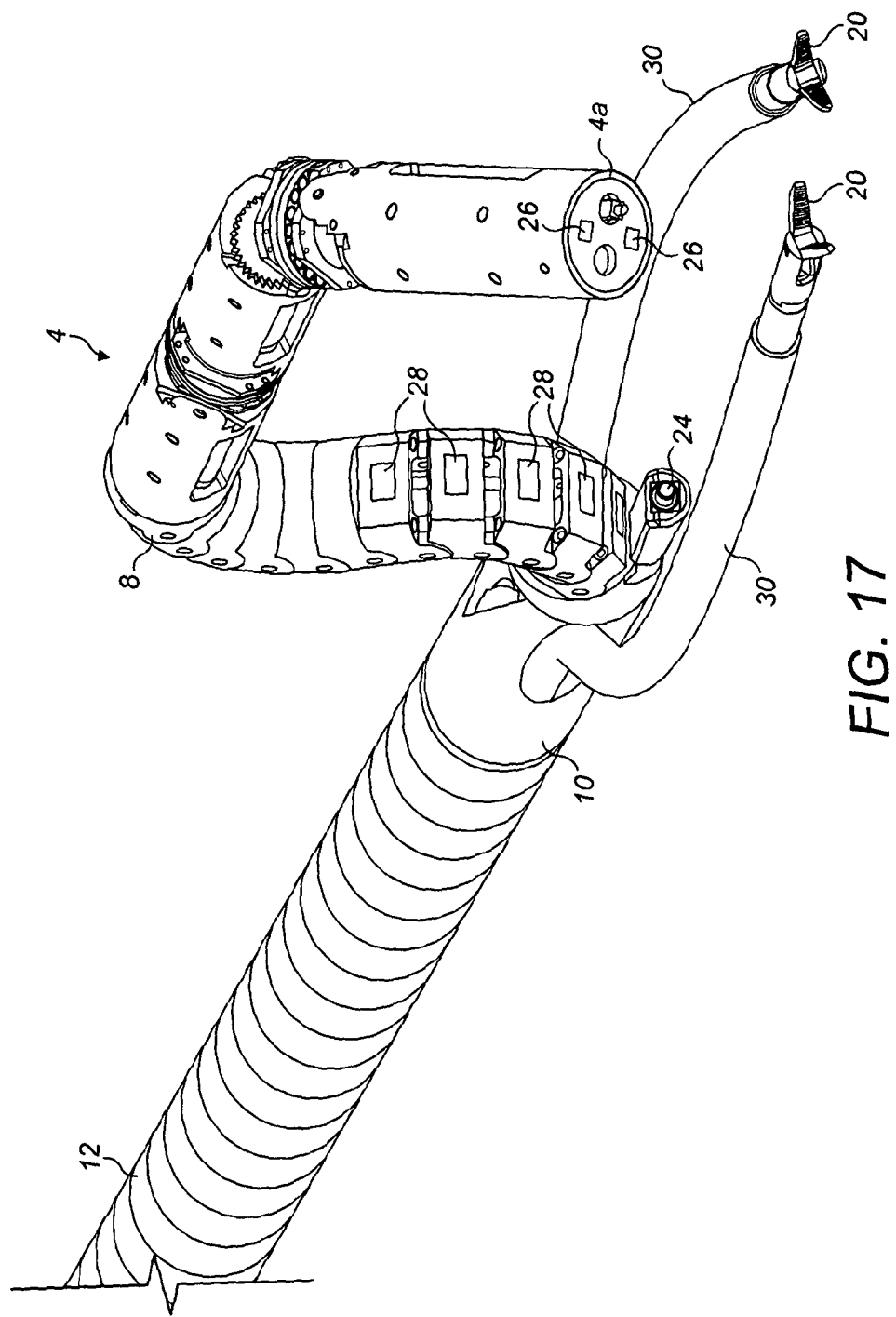
FIG. 17 is a schematic representation showing in more detail lights and cameras forming part of the device of FIG. 1.

Turning now to FIG. 17, the positions of cameras 22, 24 and LEDs 26, 28 are shown in more detail.

In the embodiment shown in FIG. 17 the device comprises five LEDs 28 positioned towards a proximal end of the flexible section 8 and two LEDs 26 positioned at a distal end of the active portion 4.

The power of the distal LEDs 26 can be adjusted so that the illuminated field is not too bright when the distal end of the active portion 4 is close to the tissue on which the device will be operating.

Two approaches to the adjustment of the LEDs may be taken.

A first approach is by sensing the distance between the distal tip 4a and the tissue.

The second approach is by analysing images acquired from the distal camera 22.

The device comprises a proximal camera 24 and a distal camera 22.

One way of visualise the operation site is to use two cameras, one mounted at the distal tip of the active portion, and the other at a proximal end of the flexible portion 8. Such an arrangement provides a broader view of the surrounding area and enhances the visualisation of the operation site.

In the embodiment illustrated in FIG. 16, two or more cameras 22 or an advanced stereo camera can be mounted to provide stereo vision (only one is shown in the figure) in conjunction with the two LEDs 26.

The plurality of LEDs 26, 28 provide illumination from a plurality of points, the position of which is known at all times through the use of potentiometers placed within the device 2, giving complete control over the physical image formation process.

Stereo camera are traditionally autonomously employed for 3D reconstruction, where traditional algorithms are penalised by the lack of colour constancy cross views. This condition applies to endoscopic data sets, where the highly localised illumination causes colours to appear differently between the left and right video channels.

The complete setup consists of two stereo cameras on the tip of the robot with two LEDs for frontal illumination and a variable number of LEDs along the body of the robot.

The LEDs placed along the body of the robot provide illumination from multiple points whose position is known at all time through the potentiometers placed within the robot itself, giving complete control over the physical image formation process.

Stereo cameras are traditionally autonomously employed for 3D reconstruction, where traditional algorithms are penalised by the lack of colour constancy across views. This condition applies to endoscopic datasets, where the highly localised illumination causes colours to appear differently between the left and right video channels.

The LEDs physical configuration is exploited to reconstruct the 3D structure of the visualised scene by explicitly taking into account shading information. Given complete knowledge of the camera and light positional information, it is possible to correlate the perceived brightness of every point visualised with its 3D position and surface orientation according to the Lambertian formation model:

$$l(x,y)=1 \diamond n(x,y) \acute{U} E(l) R(x,y,l) S(l) dl$$

where l is the image brightness for pixel coordinates x and y, l is the known light source direction vector, n is the surface normal and the integral represents the surface reflectance properties. When at least 3 source LEDs are present in the system, it is possible to solve for the unknown surface normals and, when two cameras are present, for the unknown surface depth values using exact variational calculus methods.

Three LEDs are placed along the robot body that simultaneously illuminate the scene. To distinguish which LED is contributing to the perceived brightness, the chosen wavelengths are spaced as equally as possible along the visible spectrum: 447 nm, 530 nm and 627 nm for blue, green and red LEDs respectively. The wavelengths corresponds to the sensitivities of the RGB CCD cameras used, so that the contribution to the overall image brightness from each light source can be isolated and used together for a fully dense reconstruction of the scene.

The flexible section 8 may be driven in any convenient manner and may for example be driven using a thumb stick and an embedded button which allows toggling between the joints.

The device according to embodiments of the invention thus provides a versatile surgical device particularly suitable for use in minimal invasive surgery. The device may comprise one or more slave devices that may be controlled by a master device.

The invention claimed is:

1. A surgical device having a distal end and a proximal end, and comprising:
   a delivery portion extending from the proximal end;
   first and second instrument delivery channels formed in, and extending through, the delivery portion;
   an active portion at a distal portion of the device; and
   a plug having a proximal end and a distal end, positionable between the delivery portion and the active portion, and engageable with the delivery portion at the proximal end of the plug, and with the active portion at the distal end of the plug, to thereby releasably connect the delivery portion to the active portion,
   wherein the plug includes a first plug portion in which a first plug channel is formed and a second plug portion in which a second plug channel is formed, the first and second plug channels each defining a curved path, such that the plug channels diverge from one another towards the distal end of the plug,
   wherein, when the plug is engaged with the delivery portion, the first plug channel and the first instrument delivery channel form a single continuous first instrument channel and the second plug channel and the second instrument delivery channel form a single continuous second instrument channel, and wherein the first and second plug portions are moveable relative to one another.

2. A surgical device according to claim 1 further comprising a first instrument arm adapted to be inserted into the first instrument channel, and a second instrument arm adapted to be inserted into the second instrument channel.

3. A surgical device according to claim 2 wherein each instrument arm comprises three sections: a distal section with two directional flexibility and actuatability in two planes; a middle section with one directional flexibility; and a proximal section.

4. A surgical device according to claim 3 wherein each instrument arm comprises a superelastic Nitinol tube.

5. A surgical device according to claim 4 wherein each instrument arm is driveable by at least one tendon attachable to a distal end of the instrument arm and extending along the arm to the proximal end thereof.

6. A surgical device according to claim 5 wherein each instrument arm accommodates an interchangeable instrument.

7. A surgical device according to claim 6 wherein the interchangeable instrument is flexible while capable of delivering torque using hollow flexible multi-headed shaft.

8. A surgical device according to claim 7 comprising a third instrument delivery channel formed in the delivery portion, and a third plug channel formed in the plug, the third instrument delivery channel and the third plug channel forming a third instrument channel when the plug is engaged with the delivery portion.

9. A surgical device according to claim 7 comprising a further delivery channel formed in the delivery portion, and a further plug channel formed in the plug, the further delivery channel and the further plug channel forming a device channel.

10. A device according to claim 7 wherein the active portion comprises a deployment section and an articulated section.

11. A surgical device according to claim 10 wherein the articulated section comprises a plurality of articulated universal joints and/or single degree freedom joints.

12. A surgical device according to claim 11 wherein the articulated section comprises one or more micromotors embedded in one or more or all of the joints.

13. A surgical device according to claim 12 wherein the deployment section comprises a plurality of joints pivotally linked to one another to form a continuous flexible section.

14. A surgical device according to claim 13 wherein the flexible section comprises one or more tendons adapted to drive the flexible section between a non-deployed position in which the flexible section extends in substantially the same plane as that in the delivery portion, and a shifted, deployed position in which the flexible section extends away from the plane of the delivery portion.

15. A surgical device according to claim 14 wherein the flexible section is adapted to carry a camera and/or light sources at its proximal end.

16. A device according to claim 15 further comprising a locking mechanism for locking the flexible section in any position.

17. A device according to claim 16 wherein the delivery portion is flexible.

18. A device according to claim 17 wherein the delivery portion comprises a plurality of links arranged to allow flexible movement of the delivery portion, and a flexible material adapted to extend between the links.

19. A device according to claim 18 wherein the rotational axes between links are defined by cylindrical surfaces of the delivery portion.

20. A component for a surgical device the component comprising a delivery portion comprising first and second instrument delivery channels extending through the delivery portion, and a plug engageable with the delivery portion at a proximal end of the plug, which plug comprises first and second plug channels each defining a curved path, such that the plug channels diverge from one another towards a distal end of the plug when the plug is engaged with the delivery portion, and wherein the first plug channel and the first instrument delivery channel form a first instrument channel and the second plug channel and the second instrument delivery channel form a second instrument channel, wherein the plug comprises a first plug portion in which a first plug channel is formed and a second plug portion in which a second plug channel is formed, the first and second plug channels each defining a curved path, such that the plug channels diverge from one another toward the distal end of the plug and wherein, when the plug is engaged with the delivery portion, the first plug channel and the first instrument delivery channel form a single continuous first instrument channel and the second plug channel and the second instrument delivery channel form a single continuous second instrument channel, and wherein the first and second plug portions are moveable relative to one another.

21. A component according to claim 20 wherein the delivery portion is flexible.

22. A component according to claim 21 wherein the delivery portion comprises a plurality of links arranged to allow flexible movement of the delivery portion, and a flexible material adapted to extend between the links.

23. A component according to claim 22 wherein the rotational axes between links are defined by cylindrical surfaces of the delivery portion.

* * * * *